United States Patent [19]

Ebersole et al.

[11] Patent Number: 4,753,775

[45] Date of Patent: Jun. 28, 1988

[54] RAPID ASSAY PROCESSOR

[75] Inventors: Richard C. Ebersole, Wilmington, Del.; Jesse G. Forsythe, Jr., Media, Pa.; Frank T. Gelormini, Gibbstown, N.J.

[73] Assignee: E. I. Du Pont de Nemours And Company, Wilmington, Del.

[21] Appl. No.: 722,373

[22] Filed: Apr. 12, 1985

[51] Int. Cl.[4] .................. G01N 33/551; G01N 35/00
[52] U.S. Cl. ........................................ 422/81; 422/69; 422/100; 422/102; 422/104; 436/808; 436/809; 436/180
[58] Field of Search ............... 141/9, 100, 237, 241, 141/244; 222/330; 422/63, 65, 73, 100, 102, 99, 81, 69; 436/809, 810, 185

[56] References Cited

U.S. PATENT DOCUMENTS

| | | | |
|---|---|---|---|
| 2,684,805 | 7/1954 | McBean | 141/9 |
| 3,572,552 | 3/1971 | Guinn | 422/100 |
| 3,692,488 | 9/1972 | Schwartz | 422/68 |
| 3,895,661 | 7/1975 | Praglin et al. | 141/241 |
| 4,231,990 | 11/1980 | Jottier | 73/863.33 |
| 4,256,152 | 3/1981 | Belanger et al. | 141/244 |
| 4,477,578 | 10/1984 | Miles et al. | 422/100 |

FOREIGN PATENT DOCUMENTS 03690   4/1982   European Pat. Off. .
0131934  7/1984   European Pat. Off. .

Primary Examiner—Michael S. Marcus

[57] ABSTRACT

A system and method is disclosed for the rapid detection and (or) purification of analytes in a sample. The system makes use of a fluid receptacle containing a capture reagent and a manifold having two ports. A sample containing an analyte disposed within the fluid receptacle is subjected to a capture reagent and processed by inserting the open end of the receptacle in one port. Vacuum, gas, reagents, and wash fluids are then applied to the second port to effect rapid interaction between the capture reagent and analyte, efficient washing of the capture reagent and detection and/or collection of the analyte.

The system and method provide a rapid safe, uncomplicated means of automating processes based on affinity complexation principles. Encompassed within this category of processes are immunoassays, nucleic acid hybridization tests and affinity separations.

20 Claims, 6 Drawing Sheets

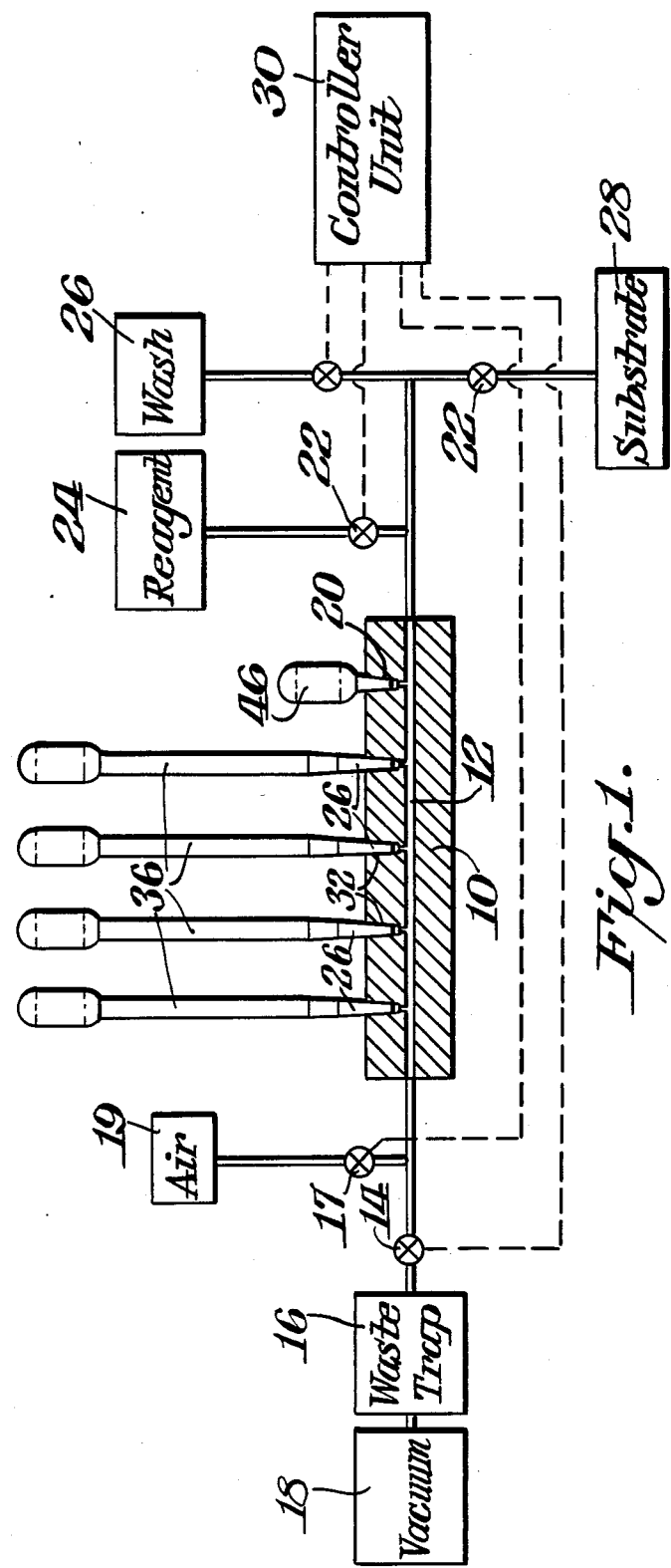

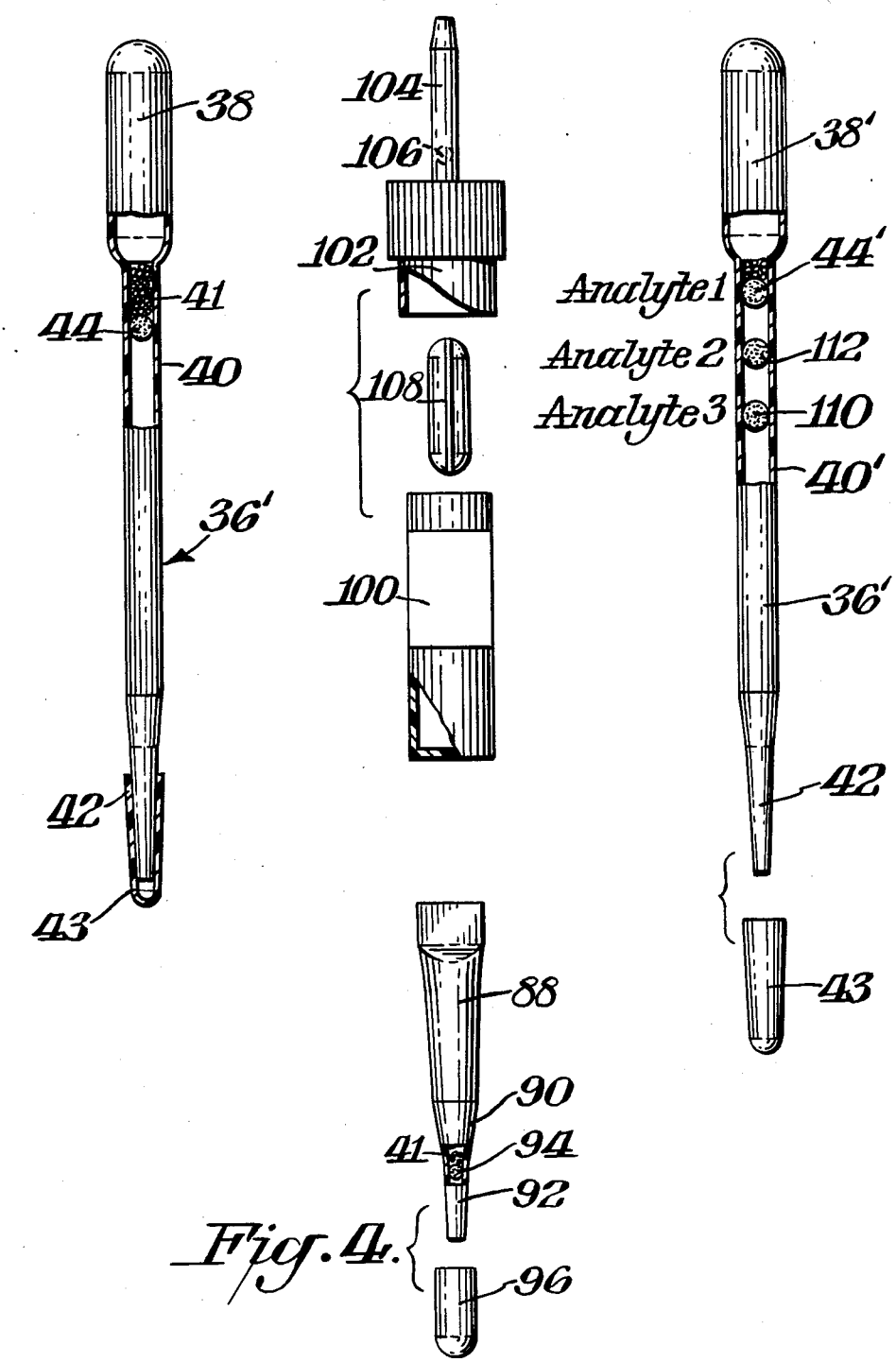

RAPID ASSAY PROCESSOR

BACKGROUND OF THE INVENTION

This invention relates to a system, apparatus and method for processing samples and more particularly to performing (1) analytical procedures on samples based on complexation reaction principles and (2) affinity separations. Encompassed within this category of analytical procedures are tests based on immunoassay principles, nucleic acid hybridization principles, and affinity complexing principles. The complexation technology is applicable to a wide range of analytical applications including the detection of soluble antigens, cells, cellular fragments, microorganisms and their products. Encompassed within the category of affinity separations are the separations of biomolecules from complex mixtures.

Generally, the types of tests within this category of analytical procedures are procedurally complex, frequently they involve multiple reagent additions, extensive wash steps, and prolonged incubation times. These procedural complexities diminish the testing convenience. Furthermore, such tests must afford high sensitivity. In order to achieve this sensitivity, long reagent equilibration times are required in order to capture the minute quantities of analytes in samples.

Analytically, complexation based tests can be applied to a wide variety of analytes which are of diagnostic importance to clinical medicine and of investigative importance to life science research. The complexation tests are inherently sensitive and specific. However, as noted above, such tests can be labor intensive and require hours of analysis time to perform.

For example, a typical test can comprise the following generalized procedural steps. In the first step, sample fluids containing the analyte for testing is contacted with a solid phase "capture reagent"—prepared with a complexing reagent specific for the analyte of interest. The sample fluid is then equilibrated with the solid phase reagent for sufficient time to enable analyte attachment to the support. Following equilibration with the capture reagent, the sample fluid is removed and the solid phase reagent rinsed to remove excess sample materials. During this process the analyte attached to the capture support remains fixed on the surface of the capture support.

As a general rule for analytical purposes the attached analyte cannot be detected directly. A second "amplifying complexing reagent" often must therefore be added and equilibrated with the solid phase support in order to detect or visualize the presence of analyte. This equilibration must also be carried out for sufficient time to insure effective reaction with the analyte on the solid phase surface. Following equilibration, the excess "free" amplifying reagent must be separated from the "bound" amplifying reagent. This is accomplished by washing the solid phase support to eliminate the unfixed active elements. At this stage, depending on the nature of the amplifying reagent a direct reading of the active elements on the solid phase support can be taken. If a test is preferred using an enzyme or other tracer to amplify the test signal, one or more substrate reagents must first be added. Following an additional incubation period, color development can then be observed.

Unfortunately, the numerous manipulations required in performing the tests—notably during the successive reagent additions, rinsings, and incubations entail risk of errors in timing, reagent measurement, specimen identification, risk of user infection, and accidental loss of test samples. This is particularly true when the large numbers of samples are batched together at the same time. The problems encountered by diagnostic laboratories in carrying out these types of tests are thus many. Clinical laboratories must cope with large throughput of samples, interpret the significance of the results, provide a wide range of determinations, return results quickly, and ensure that each assay test is performed accurately. This must be done economically in spite of the difficulties encountered with techniques that are labor intensive, and complex when compared with other tests performed in clinical laboratory. (British Medical Bulletin, 30, 38–43, 1974).

While there are many variations by which such tests can be performed, a review of the practical and theoretical constraints are well documented and beyond the scope of this invention. To overcome these difficulties, numerous devices and automation approaches have been described in the prior art.

Currently, there are a number of automated machines which are commercially available. These types of machines make use of multi-well consumables such as microtiter plates or variations thereof. In general, these machines are useful in tests where quantitative information on analyte concentrations are required. Generally, these machines are complex and expensive.

To accommodate all of the testing functions mentioned above, the instrument designs make use of a multiple modules such as a sample application module, wash module, and plate reader or detector. Frequently, these systems are not fully automated requiring operator involvement to move the multi-well plate from one module to the next.

The most serious drawback to these types of systems results from their prolonged testing time and limited range of analytical application. Tests can require hours to days to perform. Prolonged equilibration times are requirred since the microtiter test wells provide relatively small surface area—consequently limiting the amount of complexing reagent available for reaction with the analyte. Furthermore, these systems tend to rely on simple diffusion or mechanical vibration to bring the analyte in contact with the surface of the test wells. As a consequence, equilibration generally require hours to accomplish. Test results are therefore not readily available in case of medical emergency or during the patient/physician interview.

A further limitation of these system is that they tend to be limited to immunoassay applications and not really adaptable to the newer complexation test based on DNA and RNA hybridization principles.

In order to overcome these limitations, a number of processor systems which make use of alternate test devices have been recently reported in the patent literature. For example, U.S. Pat. No. 4,071,315 issued Jan. 31, 1978 to G. Chateau discloses a processor concept which makes use of a complexing capture reagent attached to roll of porous film which is fed sequentially through a series of operational modules.

The Chateau system suffers from many of the same disadvantages as mentioned above. The system is complex depending on the function of multiple independent modules and relies on simple diffusion to effect mixing and accomplish analyte equilibration with the film reagent. A further disadvantage of this system is that the system does not provide rapid turnaround time for test results. However, once engaged, large numbers of samples can be run with high throughput.

U.S. Pat. No. 4,225,558 issued Sept. 30, 1980 to Peterson et al. describes a centrifugal technique in which a plurality of fluid test cells arranged on the periphery of a motor driven rotor. The fluids to be tested and respective reagents are introduced separately into corresponding test cells and are subsequently mixed in a reaction chamber for analysis. Introduction of the fluids is accomplished by the use of vacuum and the fluids are mixed by centrifugal force. This system has a disadvantage of requiring the use of centrifugal force which reduces the throughput of the system and renders the system unnecessarily complicated.

Another system is described in U.S. Pat. No. 4,424,279 issued Jan. 3, 1984 to Bohn et al. and U.S. Pat. No. 4,458,020 issued July 3, 1984 to Bohn et al. These patents, both assigned to Quidel, describe an apparatus for processing a cylindrical tube having an open end into which a plunger filter assembly is fitted. Beads sensitized with complexing reagent such as an antibody can be used in conjunction with the device. The operation is centered around a plunger which is depressed to mix the sample with the sensitized beads. Thereafter the reagent is added and the plunger is raised to clear the chamber of the fluids. The beads are washed in much the same way by raising and lowering the plunger. Although the system is simple in design, it suffers from the requirement that the reagents and wash fluids be added manually and that a four chambered dispensing unit and the filter tube assembly be manually moved from one position to the next in order to accomplish the assay. Operator involvement is extensive. Furthermore since the tube and filter assembly remain open during handling, the devices are subject to spillage and thus subject the user to potential contact with infectious materials.

Michael Cais and Moshue Shimoni, in *Ann. Clin. Biochem.* 18, 324–329 (1981) describes a tube device for performing immunoassays in which separation of "free" and "bound" analyte is claimed to be rapidly and safely accomplished by liquid extraction techniques. While it is not explicitly described they indicate that a simple automated instrument has been developed which processes up to 40 assay tubes simultaneously This device suffers from the disadvantage of being complex in design requiring high precision parts, and is limited in application to only those analytes which can be separated by solvent partitioning.

A device for separating plasma from a centrifugal blood sample is described in U.S. Pat. No. 4,483,825 issued Nov. 20, 1984 to Fatcher. This device includes a pipette having a filter disposed over one of the two open ends. The filter end is inserted into the tube holding the blood sample and operated like a piston to force the plasma through the filter into the pipette. Such device has not been used for complexation type testing. Furthermore, being open at both ends, the device would expose the operator to biohazardous materials.

In these prior art systems, auxiliary apparatus and equipment have been typically employed for the sequential exposure, equilibration and washing of the solid phase capture reagent. For example, a vibrator or shaker is useful to both maintain controlled uniform exposure of the reaction fluids with the capture reagent and to hasten the rate of analyte interaction with the support. In addition a centrifuge is useful and effective in the aggregation of suspended solid phase reagents following equilibration. An aspirator can then be used to facilitate the decantation of the reaction fluids from solid phase reagents. Peristaltic pumps or automated syringes are useful to add reagents and/or wash solutions. These many separate functions have not readily lent themselves to an uncomplicated single automation concept, at least in a single instrument.

A number of systems have been reported which make use of chromatographic principles to increase the efficiency of analyte capture and thus shortening the analysis time. German Patent Application No. DE3217-032-A describes an immunoassay separation process using dry chromatographic column materials. In this type of application, no automated system is described.

Other systems have been developed including those using manifold systems such as those offered by J. T. Baker and Waters, Inc. These systems are designed to speed up the flow and collection of column eluants by the use of vacuum. As such, these systems depend upon open columns in which fluid flows in only one direction. The processor consists simply of a vacuum source to suck the wash solution through the immunoreagents support. As a result, the test requires multiple tubes and considerable operator intervention to complete the test procedure.

Many flow-through type systems making use of a chromatographic type column bed for analyte capture and processing are well known in the immunoassay and bioseparation literature. However, the flow-through systems have the disadvantage that they make use columns which must be carefully packed in order to avoid both fluid channeling and the inclusion of trapped gas which may reduce fluid contact with the supports. This adds to the difficulty and cost to the manufacture of the column device. Furthermore during the process, analyte capture must be accomplished in a single pass necessitating a highly efficient column. This adds back pressure to the flow system frequently necessitating positive displacement pumps to compensate increased back pressure and insure positive fluid flow. Furthermore the simultaneous processing of multiple samples is not possible. In addition, during consecutive cycles, these systems are subject to contamination and plugging due to entrapment of particles and debris. Furthermore, reduced activity of capture reagent in the subsequent reprocessing is also observed. Sample and reagent mixing prior to equilibration with the capture support must be carried out prior to the reagents reaching the test device. This is frequently accomplished by using a long connecting tube which tends to result in contamination and requires considerable lengths of time for liquid to reach the reaction container.

Japanese Patent Application No. J58,223,758 published Dec. 26, 1983, filed in the name of Kokaietal, describes a flow-through system and circulatory reaction device which claims to overcome many of the disadvantages of flow-through systems. The reaction tube is an open tube, having an opening at both ends. A filter is used to provide a support for immobilization of antibodies or antigens in a nozzle. Positive pressure is used to force the material through the cell and to wash the solid phase capture reagents. The system is mechanically complex—requiring operation of numerous syringe pumps. The system is operated at positive pressure and therefore subject to emission or release of toxic and infectious aerosols. Furthermore, since the system makes use of a packed capture bed with fluid flow in one direction, diminished flow and increased back pressure will result from plugging.

SUMMARY OF THE INVENTION

It is therefore an object of this invention to provide an automated system which can perform many of the procedural steps required in tests based on complexation reactions (for example, antigen-antibody binding, nucleic acid hybridization, and surface adherence). Specifically, it is an object of this invention (1) to achieve test operations involving sample removal, sample equilibration with solid phase reagents, wash, reagent additions, and color development steps with no operator assistance; (2) to provide a means of actively promoting the interaction between analyte and complexing reagent. In this way, testing time can be substantially reduced without comprising the ultimate detection limit or sensitivity of the assay; (3) to provide for enhanced user safety by using a negative pressure closed system in which biohazardous material can be collected and decontaminated without operator contact with sample materials; and (4) to provide an inexpensive test system which enables multiple tests to be performed simultaneously.

This invention finds use in a system for processing samples disposed in a fluid receptacle having an open end and containing an analyte to be processed and a capture reagent on a solid support, the system including means for subjecting the analyte to the capture reagent. The invention comprises the improvement in which: the system includes a manifold and receptacle defining a closed chamber and first and second ports communicating with the chamber, means to place the open end of the fluid receptacle in fluid communication with the first port, and means for selectively introducing to and removing from the chamber and hence the receptacle through the second port vacuum, air, reagents, and wash fluids, thereby to effect rapid interaction between the capture reagent and analyte, efficient washing of the capture reagent, and detection of the analyte.

The system of this invention applies coordinated pulses of vacuum and air to the chamber and hence to the receptacle. This permits fluids to be consecutively added to the receptacle and withdrawn. The system also provides for recycling the fluids within the receptacle back and forth through the capture reagent thus affording a means of rapid interaction between the capture reagent and the sample fluids. Once the analyte is attached to the capture reagent, the wash fluids may be introduced in the same manner into the receptacle and withdrawn. In a similar manner developing agents may be introduced into the receptacle and withdrawn again.

In one embodiment, the manifold has plural receptacle ports located at equal distances from the second port. In a preferred embodiment of the invention, the receptacle may be elongated and closed at one end and open at the other, with the open end being in fluid communication with the chamber. A porous retainer is positioned in the open end and so as to retain the capture reagent trapped within the compartment. Although the capture reagent typically is disposed upon a solid support, this solid support may be either particulates (beads) or it may be attached to the porous retainer itself or to the walls of the receptacle. In a preferred embodiment of the invention, the receptacle itself is collapsible.

According to the method of this invention, samples having an analyte are processed by placing the sample in a closed receptacle, which has an access port, together with a capture reagent for the analtye. A porous retainer may be positioned in the receptacle to prevent the escape of the capture reagent. The method includes the steps of subjecting the access port and hence the receptacle to a vacuum and thereafter selectively subjecting the receptacle to reagent, vacuum, air and/or wash fluids thereby to capture, wash, and/or develop the analyte. Typically the receptacle is alternately subjected to vacuum and air to recycle the analyte and reagents back and forth across the capture reagent.

The method, apparatus and system of this invention are designed to perform a variety of tests or separations based on complexation reactions while enabling user safety is to be enhanced, operator involvement to be minimized and testing times to be substantially reduced. Complexation reactions include, antigen-antibody binding, nucleic acid hybridization and surface adherence. The test processes include sample removal, sample equilibration with a solid phase reagent, washing reagent additions, and color development steps. Testing time is reduced by providing a means of actively promoting the interaction between analyte and the complexing reagent. User safety is enhanced by employing a closed system in which biohazardous materials can be collected and decontaminated without operator contact with the sample materials. Test throughput is also enhanced by providing a system and apparatus that permits multiple tests to be performed simultaneously. The system described is one that is readily adaptable to a variety of different tests and analytical applications. These include immunoassays. DNA hybridization and affinity staining tests. Finally the method and system of this invention is adapted to perform automatically many of the tests and separations involving complexation reactions with minimal operator intervention.

These types of tests tend to be procedurally complex involving staged introduction and equilibration of sample, wash fluids, and amplifying and visualization reagents for a solid phase "capture" reagent. Some means of agitation, vibration or sonication is frequently employed during the equilibration steps to enhance the efficiency and rate of analyte interaction with the solid phase capture reagents.

Several embodiments of the receptacle are possible. They may take the form of either collapsible and non-collapsible types. In one form, the receptacle may constitute a pipette like device having a bulbous compartment at one end connected with an elongated tube. A porous plug can be positioned within the tube so as to retain certain types of solid phase capture reagents within the receptacles. Alternately the capture reagents may be attached to the porous plug itself, to particulates within the receptacle, to a packed bed disposed within the tubular portion of the receptacle, or to the walls of the tubular portion. In other forms of the invention the receptacle may constitute a hollow tube close at one end or a flexible tube-like enclosure sealed at one end.

It has been found that the configuration and position of the porous septum in the rapid capture device is surprisingly important to achieve automated capture of sample analyte. A packed column configuration is ideally suited for maximum rate of analyte capture since molecular diffusion distances are minimized. In opposition, however, the back pressure and restricted flow created by the packed bed represents an important obstacle to effective movement of fluids and air in and out of the receptacle. A packed bed, thus, prolongs the time for recycling the sample through the capture beads. Further a packed bed hinders the rapid and efficient wash of the capture beads since fluids cannot be effectively removed without air being in the pressure reservoir.

By placing the porous septum in close proximity to the pressure reservoir, i.e. so that the internal volume of the bulbous portion and the elongated passageway leading to the access port each exceed the volume of the test fluids, then the recycling process can be carried out totally within the confines of the receptacle. Furthermore the obstructions to fluid and air flow through the device are greatly reduced. This results from the fact that during the process cycle fluid moving into the device will lift and tend to break up the bed of packed capture reagent. The capture particulates therefore contribute little to the back pressure, and most importantly do not restrict the flow of air into the device. Furthermore, the capture efficiency achieved from the packed bed configuration tends to be retained, since as the fluid is withdrawn from the receptacle the loose capture particulates are quickly swept into the column chamber, and repacked. Thus, establishing an effective column bed. In this way, both restriction to flow is greatly reduced and the conditions for optimum analyte capture retained. The geometry of the bulbous portion also facilitates rapid funneling of the loose capture back into the column chamber, thus further facilitating the rapid reformation of a packed column by the capture beads during the recycling process.

In another embodiment, multiple different capture reagent supports can be integrated into the test receptacles. These can be used to simultaneously check for a plurality of different analytes in same sample. Alternately the relative ratio of test response between a plurality of supports can be used for semi-quantitation of a single analyte.

The system, method and apparatus described provide a low cost, uncomplicated means of automating the time consuming, test procedures which make use of complexation type processes. The low cost, speed and convenience provided by this invention can facilitate testing in both the doctors office as well as clinical laboratories.

BRIEF DESCRIPTION OF THE DRAWINGS

The invention may be more fully understood from the following detailed description thereof taken in connection with accompanying drawings which form a part of this application and in which:

FIG. 1 is a partial block, partial schematic diagram of a multiport processor constructed in accordance with one form of this invention;

FIG. 1A is a plan view of the manifold shown in FIG. 1;

FIG. 2 is a pictorial view, partially cutaway of receptacle constructed in accordance with one embodiment of this invention for use with the system of FIG. 1;

FIG. 3 is an exploded view of another form of receptacle that may be used with the system of FIG. 1;

FIG. 4 is an exploded view of still another receptacle that may be used with the system of FIG. 1;

FIG. 5 is a pictorial view partially cutaway of still another receptacle that may find use with the system of FIG. 1;

DETAILED DESCRIPTION OF THE PREFERRED EMBODIMENT

Figure 6:
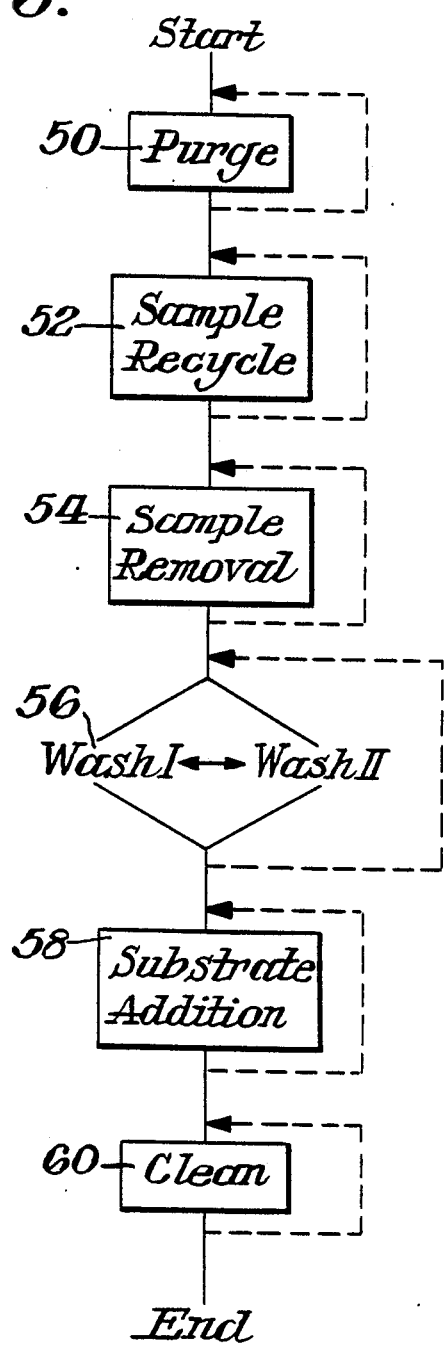
FIG. 6 is a flow diagram depicting the computer controlled method by which a complexation test is performed using the system of FIG. 1.

The system of this invention may be seen to include a multiport manifold 10, seen most clearly in FIGS. 1 and 1A, defining a closed chamber in the form of a conduit 12 extending through the manifold. One end of the conduit 12 is connected through a valve 14 and a waste trap 16 to a source of vacuum 18. Typically this source would be a vacuum aspirator or pump. A plurality of receptacle ports 20 are formed in the upper portion of the manifold 10, each being adapted to receive a suitable receptacle or other rapid assay device, as will be described. Each port is configured to provide a vacuum tight seal which affords facile insertion and removal of the receptacle. The conduit 12 is also connected through a valve 17 to a source of gas 19; typically this is air at atmospheric pressure. The other end of the conduit 12 is connected through suitable valves 22 to respective sources of auxiliary reagent 24, wash fluid 26 and a substrate 28. Each of the valves 14, 19 and 22 in turn is controlled by a suitable process control unit 30.

The seal for the ports 20 may be accomplished by configuring the ports to either have an interior taper, as shown, adapted to receive a similarly tapered receptacle tip 42 (FIG. 2) or if an exterior seal is desired, the manifold is provided with tapered stubs (not shown) adapted to fit inside a similarly tapered receptacle tip as will be described in conjunction with FIG. 8. In any event the ports 20 may be designed to accommodate a wide variety of different test devices and configurations.

The valves are preferably electronically controlled to control the access of the various fluids and sources of vacuum and air to the conduit 12. It is important in selecting the valve that they provide rapid on-off control within about 0.1 second. One suitable valve that has been found satisfactory is a pinch valve purchased from ACRO Air Associates of Concord, Calif. (Part #940121418). These valves used in combination with silicone rubber tubes for the interconnecting conduits were employed successfully in tests. Any suitable computer may be used for the controller unit 30. It need not be described further since computers of this type are well known. For example, an HP-85 computer has been successively used for this purpose. The software for such computer will be described below. The vacuum source 18 should be a source capable of providing $\geq 25$ inches of mercury vacuum. The trap 16 is useful to collect biohazardous materials. One vacuum pump which has been used successfully was purchased from SGA Scientific in Bloomfield, N.J., Part #LV-6610.

Each of the ports 20 may be in the form of a tapered recess 32 formed in the top side of the manifold 10 and communicating with the conduit 12. The manifold 10 may be formed on any suitable material that is chemically and biologically inert. Suitable materials for this purpose are polyethylene, polypropylene, or an ionomer resin such as Surlyn ® sold by E. I. du Pont de Nemours and Company.

A typical receptacle that may find use with the manifold of FIG. 1 is seen in FIG. 2 to be in the general form of a pipette having a bulbous upper portion or chamber 38 and an extended tubular portion 40. The receptacle may be formed of any of the plastic materials used for the manifold. Preferably the top bulbous portion 38 is flexible and joins the extended tubular portion 40 which is terminated in a tapered tip portion 42 which can be inserted in the taper of the manifold ports 32.

The upper chamber 38 provides a means of manually metering the fluid flow in and out of the receptacle. When and if the receptacle is used manually, by application of finger applied pressure, the user can control the amounts of sample and liquid reagents taken in and out of the receptacle. For example, test fluids may be drawn up to a precalibrated mark on the wall of the tube. In this way a measured amount of sample can be taken into the receptacle without the need for additional measurement apparatus. The upper chamber can be used for capture reagent storage. In addition, other types of reagents, i.e., antibody enzyme conjugates or other types of tag reagents may also be stored in this portion of the device. A porous retainer may be inserted into the tubular portion 40 of the receptacle to function as a permeable barrier. The pores in the retainer must be large enough not to restrict fluid flow or the entrance of cells, microorganisms, cellular fragments or particulates of interest for analysis. On the other hand the pores must be small enough to efficiently collect the capture particulate reagents. In this way the capture reagents can be efficiently retained and washed. Thus, prior to inserting porous retainer 44 into the tubular portion 40 of the receptacle, capture particulate reagents 41 are introduced into the upper chamber compartment 38. For specific applications it is desirable to combine the functions of the porous retainer and the capture absorbent. For example, this could be achieved by immobilizing capture reagents on the porous retainer or onto the walls of the column tube itself. In all cases, the capture reagent is immobilized by attachment to a solid support so that it cannot leave the receptacle.

The length of the tubular portion 40 together with the internal diameter of the tubular portion should create a volume which is equal to or less than that of the volume of the upper chamber compartment 38. Similarly the internal volume of the tubular portion 40 should exceed that of the sample of analyte and accompanying reagent fluids to be processed, i.e. the test fluid. Thus the internal volume of the receptacle should exceed the volume of the test fluid by more than a factor of two.

In an alternative embodiment, the tubular portion 40 may be packed as a column. This approach provides a means of shaping the absorbent reagents into a microcolumn for capture of sample analyte. The column compartment can also function as a second reagent compartment. The capture or reagent particulates can be added during manufacture and stored in the column chamber. The column is formed simply by forming a porous plug (not shown) at either end of the column to retain the column packing.

In still other alternative embodiments, additional chambers can be added to the device. For example, crushable ampules or blisters can be integrated in the bulb 38. In this way the reagents can be compartmentalized until the appropriate step of the testing procedure. By application of pressure the ampules or blister parts could be opened for reagent delivery.

A protective cap 43 may be inserted over the end of the receptacle if desired for reagent protection during shipment or for user protection in handling devices during testing. For example, the protective cap can be used to provide an effective moisture barrier to protect dry reagents inside the receptacle during transportation and storage. During processing it may be desirable to make use of the cap to reduce user contact with infectious or toxic sample materials which may be contained within the receptacle. Furthermore, the cap may be used to seal color formation reagents within the receptacle following testing, preventing them from leaking out during the color formation processes. The cap may be made of flexible chemically inert plastics similar to those described for the receptacle itself.

A plug 46 having a shape corresponding to the shape of the ports 32 may be used to close any manifold ports not occupied by a receptacle during test operations. The plug 46 may be formed of a suitable plastic of the same material as the receptacles.

The operation principle depends on the formation of a closed system created by inserting the fluid receptacles into ports of the multiport manifold. This forms a closed system involving coupling the interior of the manifold and the interior of the receptacles of the manifold and the interior of the receptacle or test device. Coordinated opening of the vacuum and air valves enable the operational pressure within each receptacle to be reduced or increased to atmospheric pressure. Coordinated opening and closing of the reagent, air, vacuum, substrate and wash fluid valves provides fluid access to each receptacle. Preferably, the vacuum and air are applied in pulses. The same operational force can be used to remove the fluids from the receptacles.

On application of vacuum, air or gas retained within or added to the receptacle expands providing an expansion bubble which facilitates the removal of fluid from the receptacle by "pumping" the fluid out of the receptacle. By this means two directional fluid communication can be achieved in an out of the receptacle device by application single directional vacuum force.

Fluid flow is thus achieved without the need for complicated equipment such a syringes or fluid pumps. In this way the system can be run at negative pressure. Thus fluids can be moved rapidly in both directions in and out of the receptacles through this single port by simple application of vacuum. Coordinated pulses of vacuum and air provides both the agitation of the solid phase capture reagents within the receptacle and provides a means of "active" analyte capture. Control over the vacuum in the manifold enables the sample and test reagents to be recycled back and forth through the capture reagent. This increases both the rate of analyte binding and maximizes the efficiency of analyte capture by the solid phase support. For example, the recycling process can be continued until the analyte in the sample is efficiently bound to the support. This capability not only reduces analysis time but also assures maximum testing response.

There may be seen in FIG. 6, a general processor program flow diagram by which the controller unit 30 (FIG. 1) actuates the various valves 16, 17, 22 (FIG. 1) to subject the receptacle 36 to vacuum or gas pressure or various wash or reagents. The program includes initially purging the system, as depicted by block 50, to clean the system before use. In this cycle, all of the ports 32 will be stoppered with a receptacle port plug 46 so that the system is closed. During the purge cycle, initially a vacuum from source 28 is applied to the conduit 12 as by opening the valve 14 for a period of time which may be in the order of 5 seconds. Immediately thereafter the valve 22 for the wash solution is opened with the vacuum for a short period of time, typically 0.2 second. During this portion of the cycle, wash fluid is drawn into the conduit 12 and out through the waste trap 16 to the vacuum source 18 thereby thoroughly cleansing the conduit. This cycle may be repeated several times, typically three times, during which vacuum is initially applied followed by the opening of valve 14 with one of the wash valves. Thereafter, the vacuum may be maintained for a short period of time to remove all liquids from the system, tuypically two seconds, after which the operator is given a pause command instructing him to place the receptacles into the device before proceeding further. During this pause, the receptacles 36 each containing a sample to be processed and a capture reagent capable of undergoing some type of complexation reaction, are placed in a different port 32.

Next, as depicted by block 52, the sample recycle sequence begins. During this sequence, the test fluids in the receptacle are forced successively through the capture reagent into the tubular portion of the receptacle and thence back into the bulbous compartment 38 within the receptacle. This sequence is repeated 5-10 times to affect effective interaction of the sample with the capture reagents. This process is accomplished by initially applying an increasing gentle vacuum (0.5-10 in. of Hg) to the entire system by opening the vacuum valve 14 and the air valve 17 simultaneously. The valves are then closed. After a short delay, ca. 0.5 seconds, the air valve 14 is opened for typically 5-10 seconds. This allows test fluids to flow back into the top of the receptacle. The vacuum/air valve sequence, described above, is then repeated typically 3-10 times, until effective analyte capture has been accomplished. During processing, it is important to leave some gas or air in the receptacle so that fluid may be later withdrawn as will be described below.

Next, as depicted by block 54, the sample is removed from the receptacle and passed to the waste trap 16. This must be accomplished while avoiding sample transfer between receptacles. Typically this is carried out by gradually removing the fluids from the receptacle and diluting the test fluids in the manifold chamber 10 as they are swept to the trap. Procedurally, the pressure with the receptacles is progressively reduced by repeatedly opening simultaneously the vacuum and wash valves for 0.1 second intervals. This gradually reduces the pressure within the receptacle while pulling wash fluids through the manifold to dilute and sweep the fluids into the trap 16. The sample removal cycle is then completed by application of a stronger vacuum to remove all residual fluids by repeatedly opening vacuum valve 14 for 0.5 second intervals.

Next the receptacle is washed as depicted at 56 (FIG. 6). During the wash cycle, the receptacle is subjected to vacuum by opening valve 14 for typically 5-10 seconds. Thereafter, wash fluids are injected by opening valves 19 and 22. This permits the receptacles to be filled with wash fluid. The fluid is then removed in stages by successively applying vacuum and then air to the manifold system. This alternate addition of vacuum and air distributes the fluids and suspends the capture reagents within the receptacle, this agitation insures that all internal surfaces are contacted by fluid. The alternate addition of vacuum and air is repeated several times. Finally, vacuum is applied to remove any remaining fluid in the receptacle. During this phase, trapped gas within the receptacle expands—forcing the fluid from the receptacle. The addition of air thus contributes both to increased wash efficiency and removal of fluid from the manifold system.

Next, a color formation reagent is added (block 58) to each receptacle 36 by first subjecting the entire manifold system to vacuum. Next, the substrate reagent 28 (FIG. 1) is added followed by the application of air pressure to suspend the capture particulates and force the color formation reagent into the receptacles 36. This pulsed application of air is repeated several times after which air is applied for about 10 seconds. A delay of several minutes is interposed to allow color development to take place and the receptacles to be "read". Thereafter the system is cleaned (block 60) by the application of vacuum followed by pulses of washing solution, thence vacuum. This sequence of wash solution and vacuum is repeated several times.

By selectively subjecting the receptacle to reagents, air, wash fluids and vacuum, fluid flow into and out of the device is precisely controlled and all of the essential procedural functions required for complexation processes can be achieved. Full automation of a test method is thus achieved.

The important testing advantages realized as a result of the system and method of operation, such as accelerated test response and high sensitivity, can also be achieved by using the test receptacles in a manual mode. The flexible, bulbous receptacle of this invention enables the fluids to be drawn into the device and processed manually. Thus the testing functions of sample metering, active analyte capture, reagent separation, and additional color formation reagents can be carried out manually by user application of finger force on the collapsible, bulbous receptacle. During this process, active analyte capture is also achieved by recycling the sample back and forth through the capture agent. Excess sample and reagents can then be removed and separated from the "bound" analyte by subsequent wash steps. Bound analyte can then be detected using either non-isotopic and/or isotopic-tagged reagents. The bulbous receptacle thus can perform many of the functions of both a pipette and dropper. Although the testing advantages of testing speed and sensitivity achieved with this system are retained during manual operation, the manual procedures require active operator participation and therefore is more labor intensive and subject to operator errors.

EXPERIMENTAL EXAMPLES

In order to illustrate the capabilities and advantages of the testing technology comprising this invention, three test examples are described. These include tests for group A streptococcus, herpes simplex virus (HSV) and human chorionic gonadotropin (HCG). These illustrate the analytical adaptability of the technology to the detection of soluble analytes, microbial organisms and viral materials.

Generally, reagents for the various tests were prepared as described below:

Capture Reagents

Specific monoclonal and polyclonal antibodies required for each of the tests were coupled to various particles as described below:

Ascites fluids containing monoclonal antibodies were cleared of cellular debris and lipids by centrifugation at 10,000 rpm for 40 minutes at 4° C. The ascites fluids were pooled and coupled to carbonyl diimindazole (CDI) activated agarose beads (Sigma) or coupled to CDI activated controlled pore glass particles (CPG). According to the procedures described by G. S. Bethel et al. [*J. Chrom.* 219, 353 (1981) and 219, 361 (1981)], the beads were washed free of excess antibody using PBS buffer. Prior to analysis, the beads were stored at 4° C. as a suspension in PBS buffer protected with 0.1% sodium azide.

In some instances, antibodies for specific test analytes also were coupled to chloromethyl styrenedivinylbenzene copolymer beads (30-150μ) and/or to polystyrene divinylbenzene beads (Duke Scientific Co.).

Generally, antibody immobilization on polystyrene particle types was accomplished by adding 1.0 g of core particles to 5 mL of an antibody (ca. 2 mg IgG) in phosphate (10 mM), buffered (ph 7.4) saline (120 mm) solution (PBS). The bead suspension was then sonicated for 30 seconds at 4° C. to suspend the particles and then slowly tumbled for 48 hours at 4° C. At the end of the equilibrium time, the beads were centrifuged at 2,000 RPM in a Sorvall model RC3B centrifuge for 3 minutes. The supernatant was decanted. The pelleted particles were then resuspended in a PBS buffer solution (10 ml) containing 0.1% bovine serum albumin (BSA). The particles are tumbled for 3 hours at 4° C. The capture bead reagent was then harvested by centrifugation and then washed 3 times. Each wash was accomplished by suspending the bead pellet in 10 mL of PBS buffer. The bead suspension was then tumbled for 10 minutes at 4° C. Following centrifugation, the wash fluid was removed and the bead pellet washed as described above. The antibody bead reagents were then stored at 4° C. in PBS buffer containing 0.1% sodium azide until used.

Affinity Purification of Antibody to Streptococcus

Streptococcus Group A antiserum was prepared in rabbits according to the protocol established by the Center for Disease Control. Antisera from the third bleed were pooled and utilized in the purification step. The antiserum so obtained reacted positively with streptococcal group antigens A, C, E, F, and G and did not react with B and D when tested by the Lancefield Capillary Precipitin Test. The streptococcal group antigens utilized were Difco Bacto-Streptoccal Antigen Set, Catalogue No. 2368-32, Control No. 683957.

Thirty mL of the antiserum was placed in a 0.7 cm×17 cm colum (column bed volume approximately 10.8 mL) containing N-acetyl glucosamine agarose (obtained from the Sigma Chemical Company). After removal of the unbound serum components by washing with 120 mL of PBS (prepared from 8.0 g NaCl, 0.2M $KH_2PO_4$, 2.9 g $Na_2HPO_4.12H_2O$, and 0.2 g KCl), the bound antibody was eluted with 90 mL of 3M $NH_4SCN$, pH 7.4. The fractions were collected, pooled, dialyzed extensively against PBS, and concentrated to 8.0 mL using an Amicon Model 202 Ultrafiltration cell with a YM10 membrane having a nominal molecular weight exclusion of 10,000 daltons. The final yield of immunoglobulin, assuming that a 1 mg/mL solution IgG has an absorbance at 280 nm of 1.4 O.D., was 12.8 mg. This affinity purified anti-streptococcal antibody (APSA) reacted positively only with Streptococcus A antigen in the Lancefield Precipitin Test. As control, ASPA was premixed with an equal volume of N-acetylglucosamine; no reactivity was seen with any of the Strep group antigens. When APSA was mixed with an equal volume of PBS, reactivity was seen with Strep A.

Enzyme Antibody Conjugates

Two types of enzyme antibody conjugates were used in test demonstrations. Horseradish peroxidase (HRP) conjugates were prepared using a periodate coupling procedure of NaKane (J. Histochemistry and Cytochemistry 22, 1084 (1984)). In several preparations, a modification of this procedure was used which omits the fluorodinitrobenzene blocking (Methods in Enzymology, 70, 133 (1980)).

Alkaline phosphatase antibody conjugates were prepared for test demonstration using a modification of the procedure described by E. Engavall, et al., 8, 871 (1971) and M. J. O'Sullivan, *Ann. Chim. Biochem.*, 16, 221 (1979). In a typical preparation ca. 3 unit of calf intestine alkaline phosphatase (Boehringer Mannheim Biochemicals) were dissolved in 1.2 mL of phosphate buffer (50 mM, pH 7.2) and incubated with glutaric dialdehyde (10 μL) for 50 minutes at 25° C. An antibody solution containing ca. 1.5 mg IgG in 0.2 to 0.4 mL of phosphate buffer was then added and the reaction continued for an additional 75 minutes at 25° C. At this time, the mixture was cooled in an ice bath and then placed into a Sephacryl S 200 column (2 cm×40 cm). The column was eluted with a 50 mM tris(hydroxymethyl)aminoethane buffer (pH 8.0) containing 0.1M NaCl, 1 mM $MgCl_2$ and 0.1% (w/v) Na-azide. The column elute was collected in 1 mL fractions. Fractions containing conjugate were identified by measurement of protein ($A_{280\ nm}$) and enzymatic activity with the substrate 5-bromo-4-chloro-3-indolyl phosphate (2.3 mM) in 2-amino-2-methyl-1-propanol buffer (pH 10.2) at room temperature. Prior to use the conjugate fraction was stabilized for storage at 4° C. by the addition of 10 mg/mL BSA and 0.1% Na-azide.

Affinity purified Strep A antibody-HRP (APSA-HRP) conjugates were prepared for test demonstration as follows. 8.0 mg of the APSA prepared above was conjugated with horseradish peroxidase (HRP) by the following procedure. 4 mg HRP (Sigma) in 1.0 mL of water was mixed with 0.2 mL of freshly prepared 0.1M $NaIO_4$. The mixture was stirred for 20 minutes at room temperature and then dialyzed against 1 mM sodium acetate buffer, pH 4.4, overnight at 4° C. To the retentate was added 20 μL of 0.2M carbonate, buffer, pH 9.5, and 8 mg of IgG dissolved in 1.0 mL of 0.01M carbonate buffer, pH 9.5, and stirred for 2 hours at room temperature. After this time period, 0.1 mL of freshly prepared sodium borohydride solution (4 mg/mL in water) was added and the mixture was allowed to stand for 2 hours at 4° C. This was followed by the addition of an equal volume of saturated ammonium sulfate solution, the mixture was then centrifuged, the precipitate was washed twice with 50% saturated ammonium sulfate solution and then dialyzed extensively against PBS. Bovine serum albumin was then added to a concentration of 1% and the conjugate was filtered through a Millipore filter (0.22 μm). To the filtrate was added an equal amount of glycerol. The conjugate was stored at −20° C.

Test Devices

While it is apparent to those skilled in the art that the basic components and features of the receptacle could be configured in a variety of different shapes and sizes, a serological pipet configuration was used for test examples.

Disposable serological pipets, purchased from the Centaur Scientific Co. were modified to enable integration of the porous septum and to provide a tip enabling an effective air tight seal to be formed between the tip of the test device and the processor manifold. However, prior to implacement of the porous septum, the antibody capture bead reagents (0.5 to 30 mg dry weight) were added to the device. In some instances lypholyzed conjugate reagents were also added separately or mixed with the capture reagents. Assembly of the device was then completed by insertion of a porous polyball obtained from Porex Technologies, Inc.

With several types of test reagents, it was necessary to pretreat the surfaces of the dropper device and polyball with BSA. This was accomplished by washing the internal surfaces with a 1% BSA solution in phosphate (1.0 mM) saline (120 mM) buffer (pH 7.2). In this way the surface was coated with BSA. In most instances this could be carried out before or after the capture reagents were added.

Example One (Group A Streptococcus)

Samples were obtained from throat swabs routinely submitted to the Public Health Laboratories for laboratory culture. No special instructions were given to the physicians taking the samples. No. requirements were imposed on the type of swabs used for sample collection. However, most swabs were of the Dacron ® type (Scientific Products Co.).

Upon arrival in the laboratory, the swab specimens were streaked onto sheep blood culture plates using standard laboratory procedures. Following incubation at 37° C. for 18 hours in the presence of 5% $CO_2$, the plates were examined for beta-hemolytic colonies. These findings were correlated and retained as culture reference results for comparison with the direct antigen test described below.

Once the plates were seeded, the "used" swabs were placed in a dry paper envelope and stored at $-20°$ C. until adequate numbers of specimens had been collected for testing. During this period no precautions were taken to maintain organism viability.

For test demonstration, the 50 "used" patient swabs were introduced into 0.5 mL of lytic extraction fluid prepared using a crude Streptomyces extract (W. R. Maxted, *Lancet* 225 (1948)). For convenience, a suitable extraction fluid was also purchased from Hynson Westcott and Dunning. The swabs were vortexed for 5 seconds, then incubated for 60 minutes at 37° C. Following the incubation period, the fluid was pressed out of the swab by rolling it against the wall of the test tube. The recovered swab extracts were drawn into the rapid test devices, prepared as described above, using a rabbit anti-Strep A capture reagent particles (30–130$\mu$) and a rabbit anti-Strep A alkaline phosphase conjugate.

For processing, the test receptacles were inserted into the port of the rapid assay processor (FIG. 1). The sample fluid was then recycled back and forth through the capture bed for 3 to 10 times in order to promote capture of the analyte antibody enzyme conjugate complex. This process generally requires 1–3 minutes to complete. At this stage, the sample is then automatically removed by application of vacuum. Several aliquots of wash buffer are pulsed through the interior of the processor in order to minimize sample carryover between device ports. The particles in the rapid assay devices are then washed repeatedly two to four times with 2–3 mL portions of PBS buffer. During this process, the buffer was quickly drawn into the device by first evacuating the system and then opening the wash reservoir valve. The filled tube was then partially evacuated and a pulse of air introduced to agitate the particles. During the wash phase the particles are suspended and swept throughout the interior of the receptacle device. Additional sequential pulses of vacuum and air are introduced until the fluid is completely removed from the device. The fluid removal phase of the wash cycle makes use of three staged additions of vacuum and air. An entire wash cycle can be performed in ca. 30 sec.

Following washing, enzyme substrate was automatically introduced into the rapid assay device. The devices were first evacuated and the enzyme substrate reservoir valve opened for a controlled time (0.1 sec/tube). This enables approximately 0.2 mL of enzyme substrate reagent to be introduced into the device. Pulses of air were then added, producing a brief agitation of particles and substrate reagents. For the test described herein, the enzyme substrate reagent (0.02 ml), consisting of 5-bromo-4-chloro-3-indolyl sulfate (2.3 mM) was employed.

After a period of 3–10 minutes, the color development within the tube was observed. Color intensities arising from samples exceeding that of Strep A negative control samples were interpreted as indicating a positive Strep A test result.

The results of the 50 tests performed above were analyzed by blindly comparing the findings of culture and the rapid assay technique and are as follows. In 17 cases both tests were positive, while 31 were negative by both methods. Two samples were positive by culture and antigen negative. The test results show good agreement between culture and antigen detections, thus, demonstrating that the microbial antigen detection can be performed rapidly and specifically using the rapid testing technology.

Example Two (Beta-HCG)

In order to demonstrate the system of this invention for application with soluble analytes, a test was developed for human choronic gonadotropin (HCG). For this application the following test reagents were prepared using the general procedures described above.

The HCG capture reagent was prepared by immobilizing a mixture of two monoclonal mouse IgG antibodies on plastic beads (30–170$\mu$). Each monoclonal antibody reacted with separate antigenic binding sites on the HCG molecule.

HRP enzyme (Sigma) was conjugated to a polyvalent rabbit anti-$\beta$-HCG-antibodies and was maintained in a protein matrix preserved with 0.01% thimerosal.

Urine and serum-based HCG calibrators were purchased from Organon Diagnostics.

The test was accomplished using a three-step sequence:

One mL of sample (urine or serum) was drawn into each receptacle.

Each receptacle was then inverted to dissolve enzyme conjugate reagent and suspend the capture particulate reagent. At this time, each receptacle device was then inserted in the manifold 10. Over a period of approximately one minute, the sample was recycled back and forth through the capture particular reagent employing the recycling principle described previously. At the completion, the sample was then removed by application of vacuum and the processor interior washed with pulses of washed fluid to eliminate potential sample carryover between devices. The receptacles were then washed several times to remove residue conjugate and sample remaining after the first equilibration. This was accomplished using four (ca. 2 ml) portions PBS buffer, using the procedure described above. The particle reagent agitation facilitates more efficient wash of capture reagents and thus shortens the wash time.

The enzyme substrate solution (0.2 mL), containing 1.6 mM tetramethylbenzidine (TMB), 3.3 mM urea peroxide, 0.075% sodium alginate in a 0.05M citric acid, 0.1M sodium phosphate buffer (pH 5.0), was drawn into the receptacle to immerse the capture reagent particles.

Color development required from 3 to 10 minutes at room temperature. Color intensities arising from samples exceeding that of an HCG negative sample indicates positive HCG test response.

Tests carried out with samples containing 50 mIU of HCG could be clearly distinguished from negative urine samples within 5 minutes. Furthermore, by increasing the sample contact time with the capture reagent to 5 minutes, samples containing as low as 5 mIU of HCG could readily be detected within 15 minutes of testing time. Thus, within a few minutes, sufficiently low levels of HCG can be detected to enable pregnancy to be determined within a few days to several weeks, depending on the individual, post conception.

Example Three (HSV Test)

Tests for the detection of herpes simplex virus (HSV) were performed in order to demonstrate the usefulness of the invention for the detection of viral materials.

Rabbit antibodies against herpes simplex virus types 1 (HSV-1) and 2 (HSV-2) were obtained from DAKO Corp. These were used to prepare the particulate capture reagent and an alkaline phosphatase conjugate as generally described in the reagent preparation section described above.

Viral antigen control materials were either obtained from M.A. Bioproducts (Walkersville, MD) or prepared from the supernatant of cell cultures infected with HSV. The relative amount of infective virus in the culture was determined using the standard plaque assay techniques and are referred to as plaque forming unit/mL.

The HSV type 1 and type 2 tests were performed in the system of this invention using dilutions and concentrations of the above reagents determined to produce an effective test, but are not intended to imply optimal concentrations.

HSV test and control specimens (0.5 mL) were drawn into individual receptacles. Each receptacle was then inserted into the manifold and the sample recycled approximately 5-10 times back and forth through the capture reagent. The sample was then removed. This time a pause was introduced in the processing cycle permitting the tubes to be removed and enzyme conjugate solution (0.5 mL) containing a mixture of anti-HSV I and II to be added manually, and the enzyme conjugate to be equilibrated sequentially with the capture reagent. The receptacles were then reinserted into the processor and the recycling process continued from 2-10 cycles over a period of 2-5 minutes. The conjugate solution was then removed. The receptacle contents were then washed sequentially first with 3 ml portions of phosphate buffer saline and then with buffer (pH 7.2) containing 0.5% emulphogen.

Enzyme substrate solution (0.2 mL), containing 2.3 mM 4-chloro-3-indolyl phosphate in 2-aminodimethyl propanol buffer (pH 10.2) was drawn into the receptacle. The results were then visually interpreted after a 10-20 minute equilibration.

Using this approach, samples containing 1:100,000 dilution of the M. A. Bioproducts, positive control antigen preparations were readily detected from the negative control sample containing no HSV. Likewise, HSV samples prepared from culture supernatant ca. $10^3$ plaque forming units (PFU) per mL could be identified as containing viral material.

Figure 7:
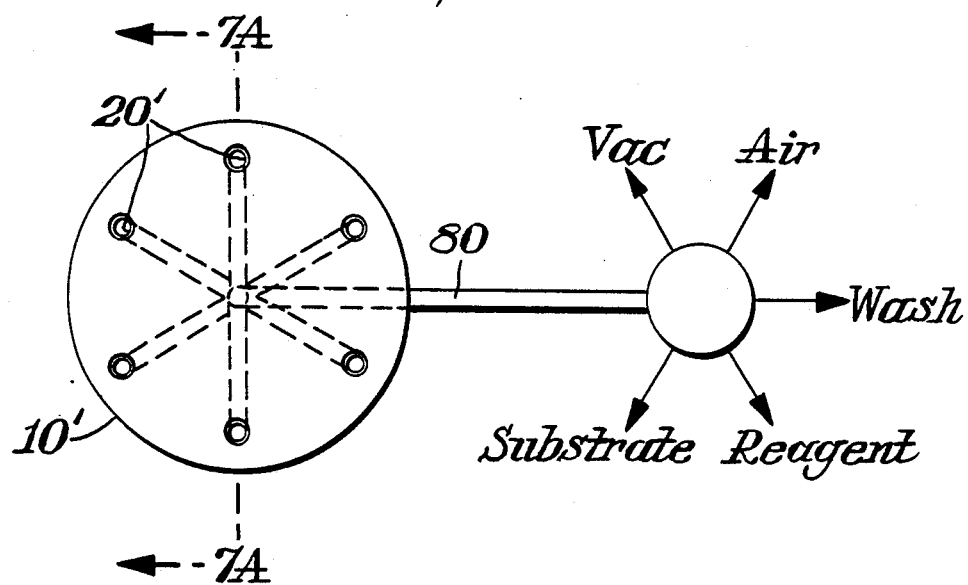
FIG. 7 is a partial pictorial, partial schematic view of an alternative form of manifold that may be used with the system of this invention.
Figure 7A:
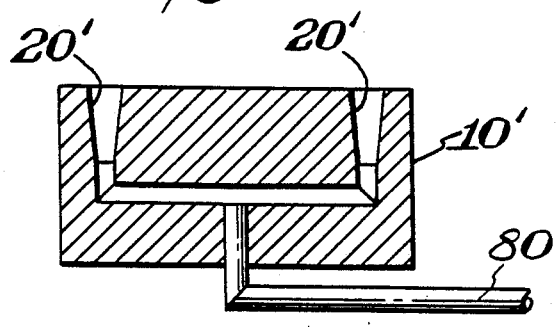
FIG. 7A is a crossectional view of the manifold of FIG. 7.

In an alternative but preferred embodiment of the system of this invention, as depicted in FIG. 7, the manifold 10' may be formed to have a single outlet connected through a conduit 80 which in turn connects to the sources of vacuum, air, wash, reagent and substrate as seen in FIG. 1. In this instance the plural ports 20' are spaced at equal distances (in this case radial from the axis of the cylindrical manifold) from the manifold cavity 82 which extends upward in the interior of the manifold along the axis. The advantages of this device is that with all of the ports 20' being at equal distances, all are subjected precisely to the same vacuum, air pressure, etc. at the same time. With that difference the operation is the same as that described in connection with FIG. 1.

In an alternative embodiment, depicted in FIG. 3, each reagent receptacle may be in the form of a vial like test tube 108. The test tube 100 has a suitable connection cap 102. An elongated tubular portion 104 enables attachment to the manifold ports 20 as previously described. A solid phase reagent 108 may be positioned in tube 100. This may assume a number of different shapes such as a ball or multi-ribbed paddle. Alternately 108 could be capsule containing reagents. The reagents may then be released by application of an appropriate stress. Since the operation and use of the receptacle embodiments all have the same characteristics as described in conjunction with FIG. 1 and FIG. 2, these need not be described further.

Other alternative embodiments of the receptacle may also be used. One such embodiment is as depicted in FIG. 4 in which the receptacle may be in the form of a flexible tube 88, having one end sealed as by crimping much in the manner as a tube of tooth paste. The lower portion of the tube 88 is tapered inwardly as at 90 so as to form an elongated tubular exit portion 92 in which a porous retainer 94 may be inserted. A protective cap 96 may be inserted over the end of the tube if desired. This tube being made in preferably of a flexible chemically biologically inert plastic similar to those described in connection with FIGS. 1 and 2.

There may be seen in FIG. 5 another alternative embodiment of the test receptacle 36'. The receptacle is substantially the same as that described in FIG. 2 having the upper pressure portion or bulbous portion 38', the elongated portion 36' with a porous retainer 44'. In this instance however, additional porous retainers 110 and 112 are positioned somewhat below the first porous plug of 44'. This permits the division of the receptacle 36' into essentially three individual sections for the simultaneous separation and/or analysis of multiple analytes from the same sample.

As illustrated in FIG. 5, the receptacle could contain three different porous capture reagents each prepared with a specific antibody. For example, 112 and 110 may contain antibody against HSV1 and HSV2 respectively. Reagent 44 would contain a non-reactivity antibody. The test response observed in each of the supports will indicate both the presence and the specific type of herpes virus. Test response on 44 will indicate the background threshold response which must be exceeded on support 110 and 112 to be indicative of a true positive result.

Figure 8:
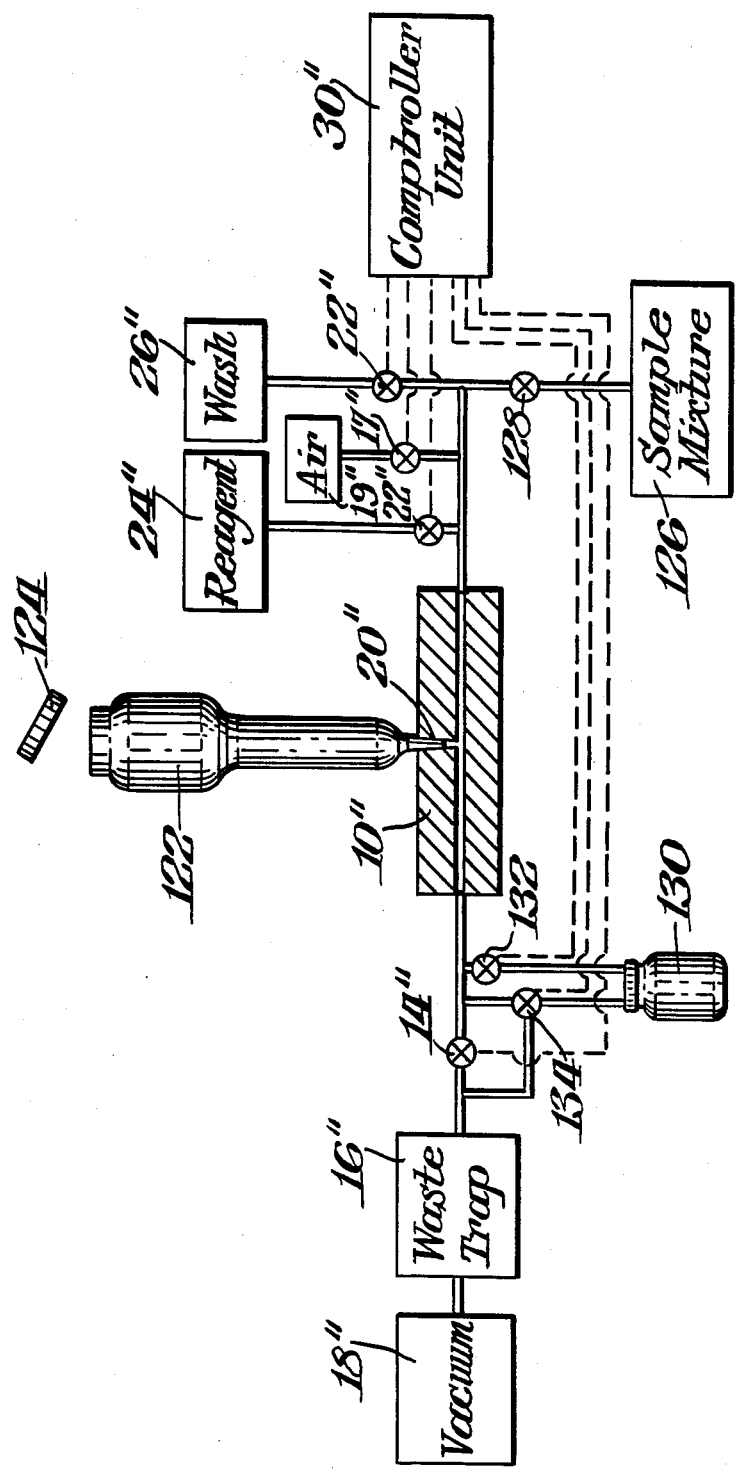
FIG. 8 is a partial block, partial schematic diagram of a multiport processor for isolating components of a complex mixture constructed in accordance with another embodiment of this invention.

An alternative embodiment of the system of this invention is depicted in FIG. 8. In this Figure there is shown a system capable of isolating specific components of a sample mixture. This system is much the same as that depicted in FIG. 1 and incorporates this vacuum source 18", a trap 16", a valve 14" for the vacuum source. The manifold 10" having ports 20" and a plug 46" to close any unused ports. The system also includes the controller unit 30" which operates the several valves including valves 22" and valves 17" and valve 14". The valves 17" and 22" control input from the reagent 24", wash 26" and a source of air 19".

Specific components of the sample may be isolated by providing a separation receptacle 122 which is much the same as the receptacles 36 of FIG. 1. The receptacle has a cap 124 which aids in loading and removing the capture reagent into the receptacle. Furthermore the cap which may have a friction fit, enables a closed system to be produced once the separation receptacle is positioned in the manifold. In the case where the manifold is configured to contain multiple ports, each receptacle may contain a different capture reagent for different components of the sample mixture which is shown as being held by block 126. The source of the sample mixture is coupled through a valve 128 to the manifold 10". A collector 130 for the purified sample is coupled through a valve 132 to the manifold and to a second valve 134 to vacuum source 18" to the trap 16".

In operation, the system of FIG. 8 makes use of the same fluid communication and ligand interaction principles described for the system design for analytical testing. The manifold is first subjected to vacuum by opening valve 14. Sample mixture is then metered into the receptacle by opening valve 128. The cycle then is much the same as that previously described wherein the sample mixture is cycled back and forth through the capture reagent to complete analyte binding. The waste sample is then removed from the receptacle 122 and collected in trap 16" by opening the vacuum valve 14". The capture reagent can then be washed to remove residual non-specific materials by opening sequentially valves 14" and 22". A desorbtion reagent is then introduced into the receptacle to release the specific affinity complexed material attached on the support. The solubilized purified ligand is then collected in container 130 by opening simultaneously valves 132 and 134. In this way the purified sample material is collected in container 130 and the capture reagent regenerated by an additional wash step.

By repeating these same sequence of steps, additional quantities of mixture can be processed and the capture support efficiently reused.

The affinity separation system comprising the above embodiment affords the advantages of rapid purifications while eliminating many of the practical constraints imposed by conventional chromatographic column based affinity purification systems.

Affinity chromatography on columns is the most frequently used technique for performing affinity purifications. Nevertheless these chromatographic based systems are subject to a number of limitations. Samples containing insoluble materials can not be used since these particulates tend to plug and contaminate the column. Loading the column with the affinity support is technique intensive and can require in excess of a day or more to degass the solvents and uniformly load the affinity adsorbent. Large quantities of affinity adsorbent are required since the most favorable purification tend to be achieved when the binding capacity of the adsorbent exceeds the sample by a factor 4 to 6. Since the chromatographic support materials can be expensive and purified ligand is required for preparation of the affinity adsorbent, the inefficient use of the adsorbent can be both expensive and may be wasteful of scarce materials. Most importantly, the excess adsorbent tends to increase the size of the column and thus increase the time for sample processing by reducing column flow rates. In addition during deadsorption, the purified sample tends to be diluted. Expensive supporting equipment such as column monitors and fraction collectors must also be used to locate and collect the purified sample.

The operational principles described herein provide for a low cost, fully automated rapid purification system which retains the advantages of affinity purifications without the limitation imposed by chromatographic column based systems. As described above, the systems makes use of a non-packed loose adsorbent. High sample throughput and rapid sample interaction with the support can thus be obtained by drawing the sample into the receptacle. The capture support thus is suspended in a fluidized bed like suspension. This greatly reduces backpressure, thus increases the fluid flow while still providing for efficient interaction with the sample. As the fluid is then withdrawn, the capture support settles into a packed bed configuration further facilitating rapid kinetics of interaction between the support and sample ligand. The efficiency of interaction in both the "fluidized bed" and "packed bed" configuration is further increased by recycling the sample back and forth through the affinity support. Thus the rate of sample interaction can be maximized while minimizing reduction in flow due to backpressure. Loading the affinity support into the receptical can be performed quickly and conveniently simply by pouring the support into the receptacle. The time consuming procedure of degassing solvents and packing the column are therefore unnecessary. Furthermore, during desorbtion of the purified sample from the support, the purified material is maintained as a concentrated solution and collected in a single container. The need for expensive support equipment such as pumps, column monitors and fraction collection equipment is thus rendered unnecessary. Because of the rapid fluid communication with the receptacle, the adsorbent can be quickly regenerated. This enables the affinity adsorbent to be repeatively reused over and over again. In this way the amount of adsorbent can be significantly reduced. Most importantly, all of the steps of sample introduction, sample equilibration, support washing, elution of the purified sample and regeneration of the support are conveniently performed and controlled by the system, thus providing a low cost, automated system providing high sample throughput and user convenience.

Figure 9:
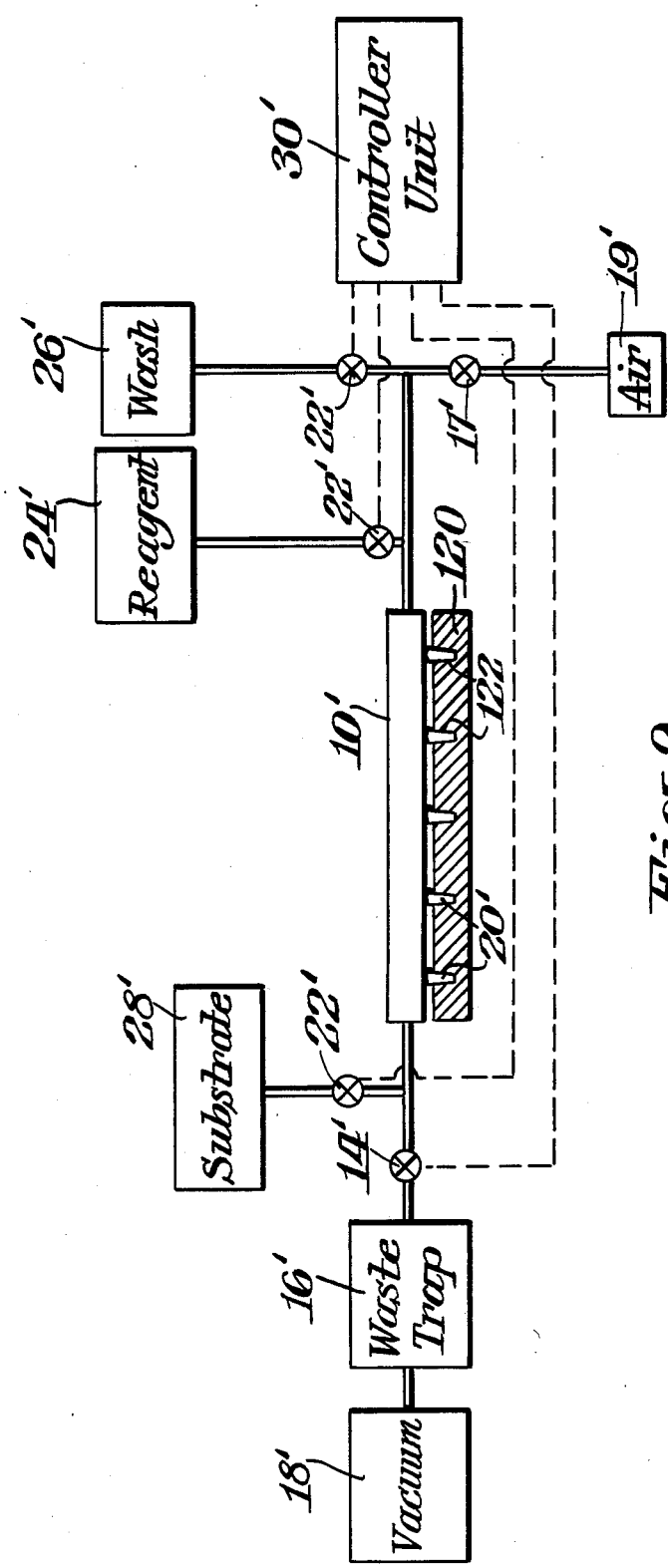
FIG. 9 is a partial pictorial, partial schematic diagram of the system of this invention modified to find use with a microtiter plate.

In FIG. 9 there is depicted another alternative embodiment of the system depicted in FIG. 1. The system of FIG. 9 is substantially the same as that depicted in FIG. 1 with the exception that the manifold is modified. The manifold 10' is modified to be capable of working with a microtiter plate 120. The microtiter plate 120 is formed with a plurality of cavities 122 formed therein. Correspondingly, the manifold 10' is formed such that each of the ports is in the form of a stub 20' capable of mating with the respective cavities 122 of the microtiter plate 120. The stubs 20' may be slightly tapered so as to fit within the cavities 122 with a slight friction fit to provide a closed cell receptacle or cavity. Thus, in each of the cavities of the microtiter 122 of the microtiter plate is filled with whatever reagents are deemed necessary along with the capture reagents beads and the sample analyte to be processed. The microtiter plate is then fitted over the cavities 122 each over the different stub 20'. From this point on, the processing is substantially identical to that described in connection with the system of FIG. 1 and need not be repeated. Alternatively, a flat mating seal may be provided for the stubs 20'.

In accordance with the subject invention, a simple sensitive technique is seen to be provided for the visual determination and purifications of analytes at extremely low concentrations using an uncomplicated procedure and device without the requirement for supporting apparatus or equipment, which may not be available routinely at home or in the doctor's office. It is the further capability of the invention to provide a receptacle with premeasured, self-contained reagents. The subject invention also provides for approaches for achieving rapid analyte capture and detection such as sample recycling and using a fluidized suspended particle reagent bed.

The capability to store, add reagents during the test procedure, and to effect wash of the capture reagents significally adds to the testing versatility of the system. For example, virtually all immunoassay test procedures can be effectively performed in the device. Test protocols based on competitive equilibrium, sequential saturation, immunometric, sandwich, and tandem reaction principles can be employed. Furthermore, test protocols based on immobilized antigens and non-immunochemical capture supports can also be carried out. For example, hybridization tests which rely on the use of DNA and RNA probe can be employed.

Furthermore another application which the system could be adapted to is the detection of bacteria in urine samples. This would be based on a simple staining technique in which the bacteria are collected on particulate supports and stained with a conventional immunological or bacteriological stains.

The system, method and apparatus described provide a low cost, uncomplicated means of automating the time consuming test procedures normally required for complexation type tests. The low cost, speed and convenience provided by this invention can facilitate testing in both the doctors office as well as clinical laboratories.

What is claimed is:

1. A system for processing a sample, containing an analyte to be determined, in a fluid receptacle, the receptacle containing a capture reagent for the analyte, the system comprising:
   a manifold, defining a closed chamber, having a first port on an upper portion of the manifold and a second port, both ports communicating with the chamber.
   a fluid receptacle having a solid support for the capture reagent, having a single open end and an enlarged bulbous portion opposite the open end, and being adapted to receive the sample, the capture reagent being disposed on the solid support,
   means adapted to detachably mount the fluid receptacle above the manifold with the open end below the remainder of the receptacle and in fluid tight communication with the first port, and
   means for selectively introducing to and removing from the chamber and hence the receptacle through the second port vacuum, gas, reagents and wash fluids, thereby to alternatively effect rapid interaction between the capture reagent and analyte, efficient washing of the capture reagent, collection of the analyte, and cleaning of the closed chamber.

2. The system of claim 1 in which the introducing means applies coordinated pulses of vacuum, fluids, and air to the chamber to control both the direction of fluid movement within the receptacle and to effect fluid communication between the chamber and the receptacle, and includes means for maintaining the chamber at subatmospheric pressure.

3. The system of claim 2 which includes a plurality of fluid receptacles and wherein the manifold defines plural first ports communicating with the closed chamber, each adapted to detachably receive and to place a different fluid, with the open end below the remainder of the receptacle, in fluid tight communication with the chamber, thereby to simultaneously permit the plural fluid receptacles to be subjected to the vacuum, gas, reagents and/or wash fluids.

4. The system of claim 3 in which the plural first ports are located at equal distances from the second port.

5. The system of claim 1 which includes a plurality of fluid receptacles and wherein the manifold defines plural first ports communicating with the closed chamber, each adapted to detachably receive and to place a different fluid receptacle, with the open end below the remainder of the receptacle, in fluid tight communication with the chamber, thereby to simultaneously permit the plural fluid receptacles to be subjected to the vacuum, gas, reagents and/or wash fluids.

6. The system of claim 5 in which the plural first ports are located at equal distances from the second port.

7. The system of claim 2 which includes means to collect waste fluids disposed between the second port and the vacuum means.

8. The system of claim 2 wherein the fluid receptacle bulbous portion is closed defining a compartment and has a porous retainer in the open end, the capture reagent being disposed in the compartment.

9. The system of claim 8 wherein the solid support is in the form of particulates that cannot pass through the retainer.

10. The system of claim 8 wherein the solid support is the porous retainer.

11. The system of claim 1 wherein the fluid receptacle bulbous portion is closed defining a compartment, and has a porous retainer and the solid support positioned in the open end.

12. The system of claim 11 wherein the fluid receptacle compartment is collapsible.

13. The system of claim 11 wherein the closed chamber is in the form of an elongated passageway with the second port disposed at one end of the passageway and which includes a third port disposed at the other end of the passageway.

14. A test apparatus for processing samples, the test apparatus comprising:
- a fluid receptacle having a single access port and a solid support, a capture reagent disposed on the solid support, an enlarged bulbous portion opposite the access port, and adapted to contain a sample having an analyte to be processed,
- a closed manifold having a first port on an upper portion of the manifold adapted to detachably receive the access port of the receptacle and place it in fluid tight communication with the manifold and a second port, the receptacle being positioned above the manifold, with the access port being positioned in the first port, the second port being located below the first port,
- means to selectively subject the manifold through the second port to vacuum, gas, reagents, and wash fluids,
- the receptable forming with the manifold a closed system, whereby the sample can be selectively subjected to the vacuum, gas, reagents and wash fluids.

15. The apparatus set forth in claim 14 which includes a plurality of the receptacles and in which the manifold has a plurality of first ports each adapted to detachably a different receptacle and place it in fluid tight communication with the manifold.

16. The apparatus set forth in claim 15 in which the first manifold ports are located at equal distances from the second port.

17. The apparatus of claim 16 wherein each fluid receptacle bulbous portion is closed defining a compartment, and has a porous retainer and the solid support positioned in the open end.

18. The apparatus of claim 17 wherein the selective subjecting means includes a separate valve for coupling sources of each of the vacuum, gas, reagents and wash fluids with the manifold, and a controller for selectively actuating the valves in concert to introduce and withdraw the air, vacuum, wash fluids and reagents into and from the receptacles.

19. The apparatus of claim 15 wherein each fluid receptacle bulbous portion is closed defining a compartment, and has a porous retainer positioned between the access port and the bulbous portion.

20. The apparatus of claim 19 wherein the selective subjecting means includes a separate valve for coupling sources of each of the vacuum, gas, reagents and wash fluids with the manifold, and a controller for selectively actuating the valves in concert to introduce and withdraw the vacuum, air, wash fluids and reagents into and from the receptacles.

* * * * *